(12) United States Patent
Moor et al.

(10) Patent No.: US 6,320,104 B1
(45) Date of Patent: Nov. 20, 2001

(54) MULTILEAF LETTUCE

(75) Inventors: Cornelis Marinus Moor, Monster; Jurjen Johannes Berg, Ulvenhout, both of (NL)

(73) Assignee: Rijk Zwaan Zaadteelt en Zaadhandel B.V. (NL)

( * ) Notice: Subject to any disclaimer, the term of this patent is extended or adjusted under 35 U.S.C. 154(b) by 0 days.

(21) Appl. No.: 09/254,817

(22) PCT Filed: Jul. 15, 1998

(86) PCT No.: PCT/NL98/00412

§ 371 Date: May 28, 1999

§ 102(e) Date: May 28, 1999

(87) PCT Pub. No.: WO99/03329

PCT Pub. Date: Jan. 28, 1999

(30) Foreign Application Priority Data

Jul. 15, 1997 (NL) .................................................. 1006588

(51) Int. Cl.⁷ .............................. A01H 5/00; A01H 5/10; A01H 1/00

(52) U.S. Cl. ............................................. 800/305; 800/260

(58) Field of Search ..................................... 800/305, 260, 800/270, 298, 258

(56) References Cited

U.S. PATENT DOCUMENTS 4,003,156  1/1977  Sibi et al. .

OTHER PUBLICATIONS

Abdel–Razik. Alexandria JJournal of Agricultural Research, vol. 41, No. 2, pp. 359–368, 1996.*
Eenink et al. Research on the inheritance of fasciation in lettuce (Lactuca sativa L.), Euphytica, vol. 29, pp. 635–660. (Abstract only), 1980.*
Eskins et al. Journal of Plant Physiology, vol. 147, No. 6, pp. 709–713, 1996.*
Haque et al. Genetica Iberica, part 38, pp. 139–155, 1986.*
The New Royal Horticutural Society Dictionary of Gardening, Ed. Huxley, Macmillian Press Limited, London, vol. 3, pp. 53–54, 1992.*
Eenink, A.H. et al. "Research on the inheritance of fasciation in lettuce (Lactuca Sativa L.)," Euphytica 29, 1980, pp. 653–660.
White, Orland E., "Fasciation," The Botanical Review, vol. XIV, No. 6, pp. 319–358, Jun. 1948 (The Blandy Experimental Farm and Miller School of Biology, University of Virginia).
Haque, M.Z. et al., "Effects of Seed–Irradiation in Lactuca and Cichorium," Genética Ibérica, part 38, 1986, pp. 139–155.
Sahu, G.R. et al., "An induced fasciated mutant in safflower," Science and Culture, vol. 44, No. 9, 1978, pp. 405–406 (abstract).
Bowring, J., "A preliminary note on fasciation in lettuce," Journal of the National Institute of Agricultural Botany, vol. 13, No. 2, 1974, pp. 210–216 (abstract).

* cited by examiner

Primary Examiner—Gary Benzion
Assistant Examiner—Melissa L. Kimball
(74) Attorney, Agent, or Firm—Webb Ziesenheim Logsdon Orkin & Hanson, P.C.

(57) ABSTRACT

The invention relates to a new characteristic of lettuce which is referred to as multileaf characteristic and comprises the capacity to cause the formation in lettuce plants with a determined leaf morphology at the ready-to-harvest stage of significantly more leaves than in lettuce plants with the same leaf morphology which do not contain the characteristic. The term "significantly more" comprises: at least 1½ times as many as a lettuce type with a comparable leaf morphology, preferably at least twice as many, more preferably at least 2½ times as many, most preferably at least 200 leaves, at a ready-to-harvest stage and a determined head weight. The invention further provides a lettuce plant of the genus Lactuca in addition to a lettuce plant of the species *Valerianella locusta* L. (lamb's lettuce), both with the multileaf characteristic, seed of such lettuce plants and heads of lettuce.

7 Claims, 7 Drawing Sheets

MULTILEAF LETTUCE

The present invention relates to a new head form characteristic in lettuce, to use of the new characteristic in the development of new types of lettuce plant which differ morphologically from the lettuce plants known heretofore, and to heads of lettuce which contain this characteristic and thereby differ morphologically from known heads of lettuce.

A great diversity of lettuce varieties exists nowadays. At present more than a thousand cultivars are known which can be divided roughly into the groups butterhead lettuce, iceberg lettuce, batavia lettuce, cos lettuce or romaine lettuce, oakleaf lettuce and lollo lettuce. This classification is based on the morphology of the leaf and the degree of head forming. However, other classifications are used in addition to this one. The UPOV list of descriptions of lettuce varieties thus refers for instance to the following six groups: butterhead lettuce, crisp lettuce, cos lettuce, "Grasse" lettuce, cutting lettuce and stem lettuce.

The known head lettuce, also known as butterhead lettuce, and the iceberg lettuce have the drawback that in these types of lettuce the outer leaves of a head of lettuce are clearly much larger than the inner leaves. For applications wherein cut or peeled whole leaves are used, such as in sandwiches, on hamburgers and the like, leaves of the most uniform possible size are preferred. In the case of heads of lettuce with a clear heterogeneity in leaf size, such as the head-forming lettuce types butterhead lettuce or head lettuce, iceberg lettuce, batavia lettuce, cos lettuce or romaine lettuce, and "Grasse" lettuce, the outer large leaves will either be unusable or will always have to be reduced in size before use by means of cutting or tearing. Browning occurs quite quickly on the cut or torn edges whereby the lettuce loses its attractive appearance and rotting can also occur more rapidly. Similar problems occur in automatic processing into cut lettuce.

It is the object of the invention to provide a new type of lettuce with which the above described problems can be avoided.

According to the invention a type of lettuce is now provided which, in comparison with the known types of lettuce, comprises significantly more leaves of substantially equal dimensions at the ready-to-harvest stage. "Of substantially equal dimensions" is understood to mean that the leaves of this so-called multileaf type have on average a shorter length and lower weight relative to a normal lettuce plant with a comparable leaf morphology and comparable plant weight.

In the case of butterhead lettuce of the new type, due to the significantly higher number of leaves and the average shorter leaf length, a large number in absolute sense, and a large part in relative sense, of the harvestable leaves falls within the size of 4 to 12 cm leaf length (see Table 1).

Lamb's lettuce of the new type (*Valerianella locusta* L.) likewise has more leaves which have a smaller leaf size than lamb's lettuce plants not having the characteristic according to the invention (see Table 4).

"Significantly more leaves" is understood to mean in this case at least 1½ times as many as a type with a comparable leaf morphology at equal (or comparable) plant weight, preferably at least twice as many, more preferably at least 2½ times as many, most preferably at least 200 leaves of substantially equal dimensions.

The lettuce provided according to the invention is per se a new type but can have different leaf morphologies which in turn originate from other types of lettuce. The type of lettuce according to the invention is however always "multileaf" lettuce.

The characteristic "significantly more leaves of substantially equal dimensions" is a new head form characteristic and will be further designated "multileaf" characteristic and likewise form part of the invention. The presence of the multileaf characteristic in a lettuce plant can be determined simply by comparing the total number of leaves of a ready-to-harvest lettuce plant suspected of possessing the multileaf characteristic with the total number of leaves of a ready-to-harvest lettuce plant which is comparable in respect of leaf morphology and plant weight but which certainly does not possess the multileaf characteristic (control plant). When the suspected multileaf lettuce plant has at least 1½ times as many leaves as the control plant, it can be stated that the multileaf characteristic is present. In such plants use is in that case made of the characteristic according to the invention. Use has also been made of the characteristic in the manufacture of such plants. These types of use also form part of the invention.

The multileaf characteristic means in fact that plants have a genetic constitution which enhances the occurrence of fasciation at a determined stage of the vegetative growth. Fasciation in butterhead lettuce occurs at a relatively early stage of the vegetative growth, while in lamb's lettuce the characteristic is expressed only at a later stage of growth.

Fasciation, also referred to as band formation, is a per se undesired phenomenon which can occur in many types of vascular plants. It was already described in 1948 by White in "Fasciation", Bot. Rev. 14, 319–358 (1948). Fasciation in lettuce is characterized by the apex of a stem becoming increasingly wide when it begins to lengthen. A cone-shaped apex normally results. In the case of fasciation however, a flat, wide and comb-like (grooved) band of meristematic tissue is formed. It is known that fasciation in lettuce has a genetic basis and is inherited recessively (Haque & Godward, Genetica-Iberica 38, 139–155 (1986)) or additively (Eenink & Garretsen, Euphytica 29, 653–660 (1980)). In addition, influences of environmental conditions on the expression of fasciation have also been described (Eenink & Garretsen, supra).

Fasciation in lettuce is a phenomenon which has been known for some time and which was long considered mainly as disadvantageous, because lines submitted for registration under the UPOV Treaty often did not react uniformly to fasciation and because fasciation hinders seed production. Fasciation does however also have a positive side, since fasciated plants are slow-bolting, which is a particular advantage for greenhouse varieties in the summer period.

According to the invention the phenomenon of fasciation has now been used to arrive at an entirely new type of lettuce. By specific selection it has been possible to increase, respectively advance the degree and the time of fasciation, whereby a fasciated apex is already formed, for instance in butterhead lettuce, at a very early stage of the vegetative growth. The final lettuce plant hereby acquires a rosette-like head which is built up of a very large number of leaves of substantially equal size on a greatly enlarged stem base.

In lamb's lettuce the characteristic occurs later, but at the harvestable stage the differences from lamb's lettuce plants not displaying the characteristic is very clearly visible.

The advantage of the new lettuce plants according to the invention is that a very large number of leaves of substantially equal dimensions can be cut from one head of lettuce. Moreover, owing to the greatly increased circumference of the stem, the leaves can be cut from the stem at the location of their petiole more easily than in lettuce types with a comparable leaf morphology. Only a limited cut surface hereby results and the leaves them-selves remain intact.

Owing to their substantially equal dimensions, the leaves are particularly suitable for use on for instance sandwiches or hamburgers, or in pre-cut salads.

In lamb's lettuce the multileaf characteristic results in a different manner of growth. In lamb's lettuce not displaying the multileaf characteristic (further referred to as "normal" lamb's lettuce) the leaves are crossed in pairs. In the multileaf lamb's lettuce the leaves are placed in groups as rosettes. The head consists of large numbers of such rosettes.

Described and shown in the accompanying examples and figures as illustration of the invention are the obtaining (example 1), the degree of expression and inheritance (example 2) and the appearance (figures) of a head of lettuce with a leaf morphology of butterhead lettuce. Example 3 shows the differences between "normal" lamb's lettuce and lamb's lettuce according to the invention.

The multileaf characteristic can however also be combined with characteristics of other types of lettuce, such as leaf shape, leaf thickness, serration, leaf colour and leaf consistency (for instance crispiness). These characteristics can be transferred from other lettuce types to the type described herein. This transfer can take place by means of recombinant DNA techniques and/or by conventional crossing-in. The variants which result in this manner likewise fall within the scope of the present invention.

"Leaf morphology" is understood to mean the whole of the phenotypical characteristics which provide a leaf with the appearance characteristic of the associated lettuce type.

Figure 1:
FIGS. 1–3 show respectively the top, bottom and cross-section of a head of multileaf butterhead lettuce according to the invention. By way of comparison.
Figure 2:
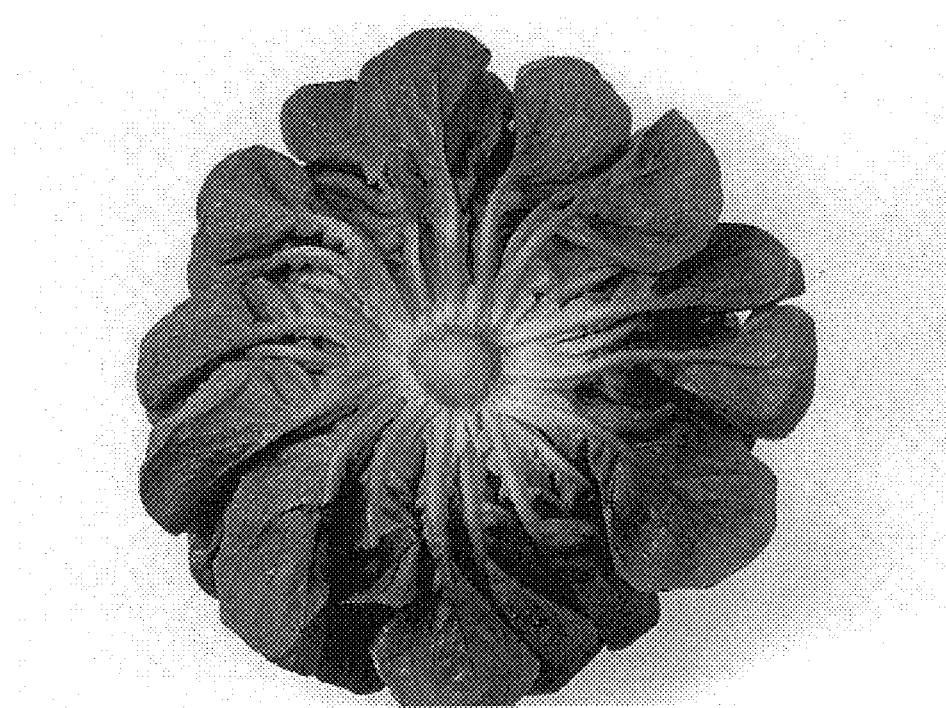
Figure 3:
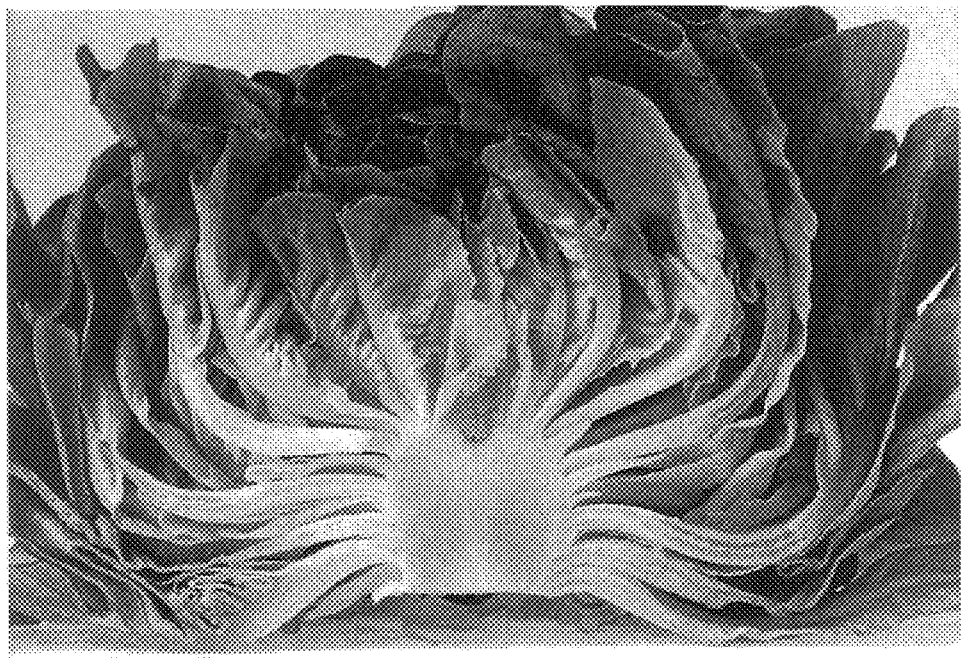
Figure 4:
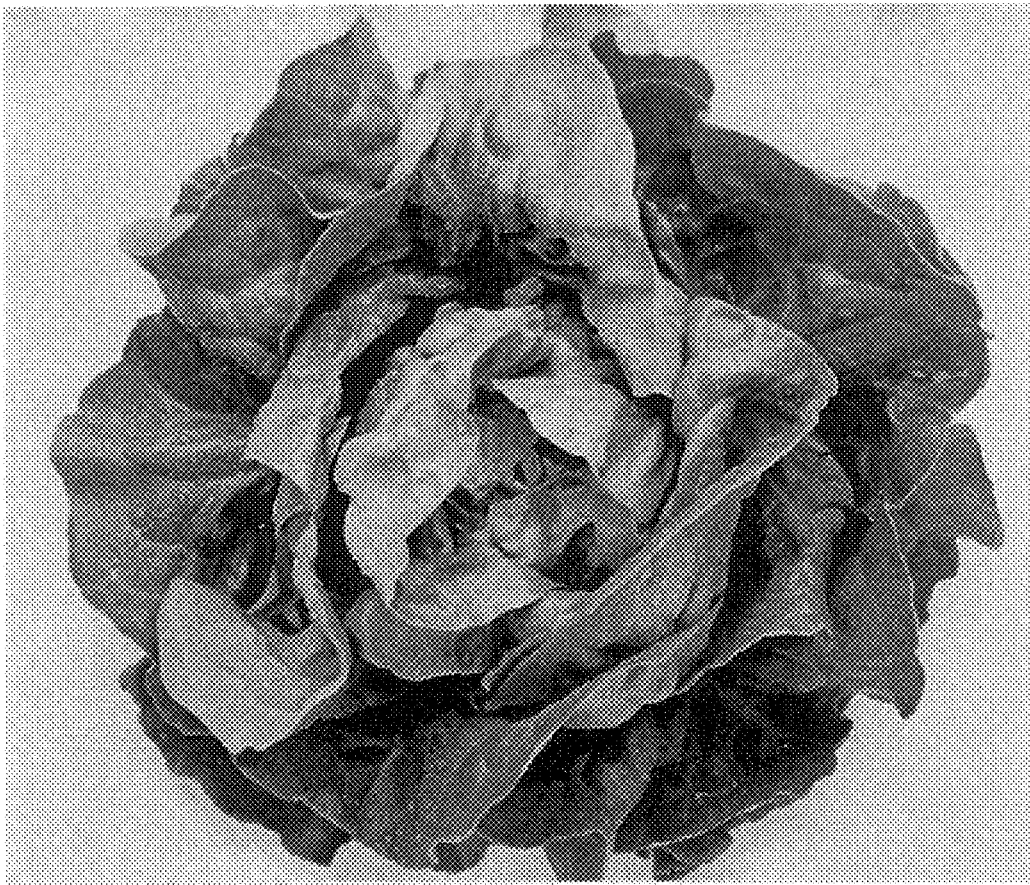
FIGS. 4 and 5 show top and bottom views of a head of butterhead lettuce. On the underside of the head of multileaf lettuce is clearly visible that the head possesses a larger number of leaves of smaller dimensions than the head of butterhead lettuce.
Figure 5:
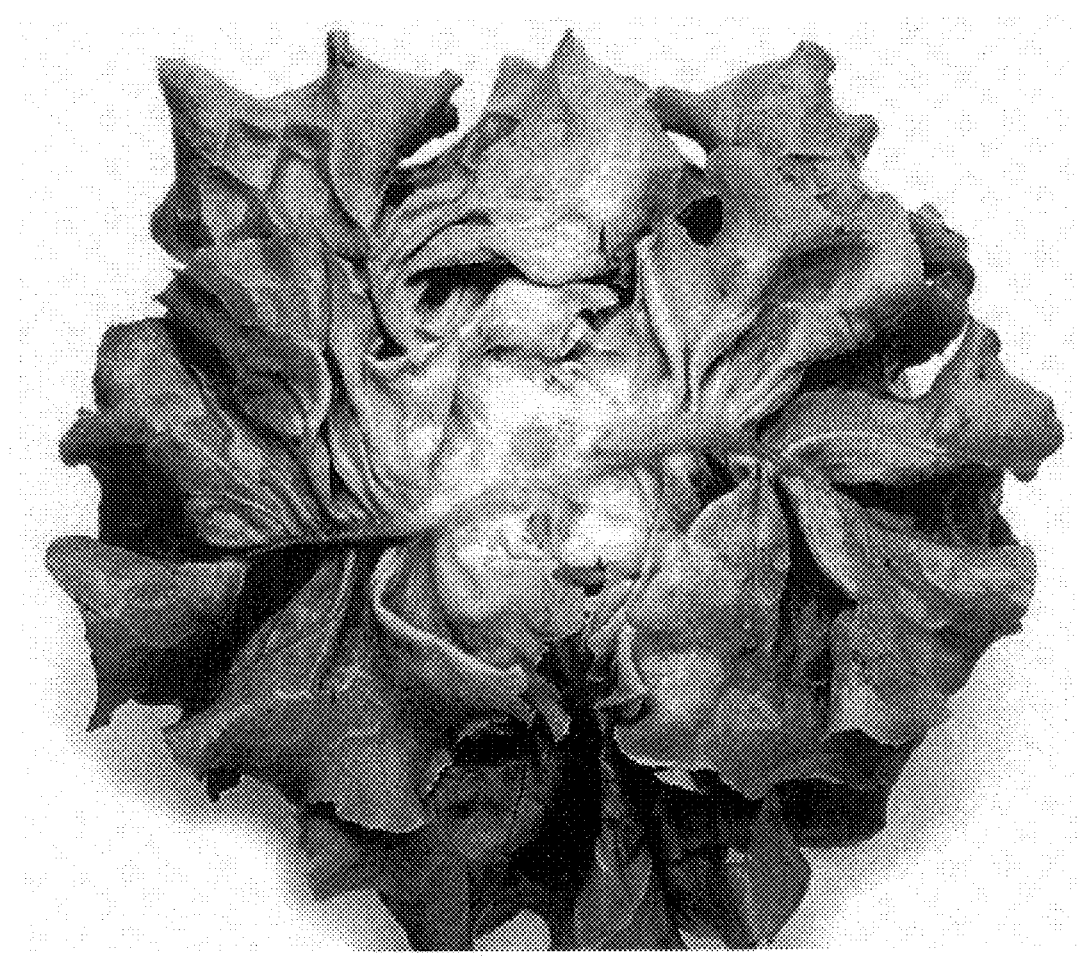
Figure 6:
FIG. 6 shows a typical head of multileaf lettuce from which the stem base has been removed.
Figure 7:
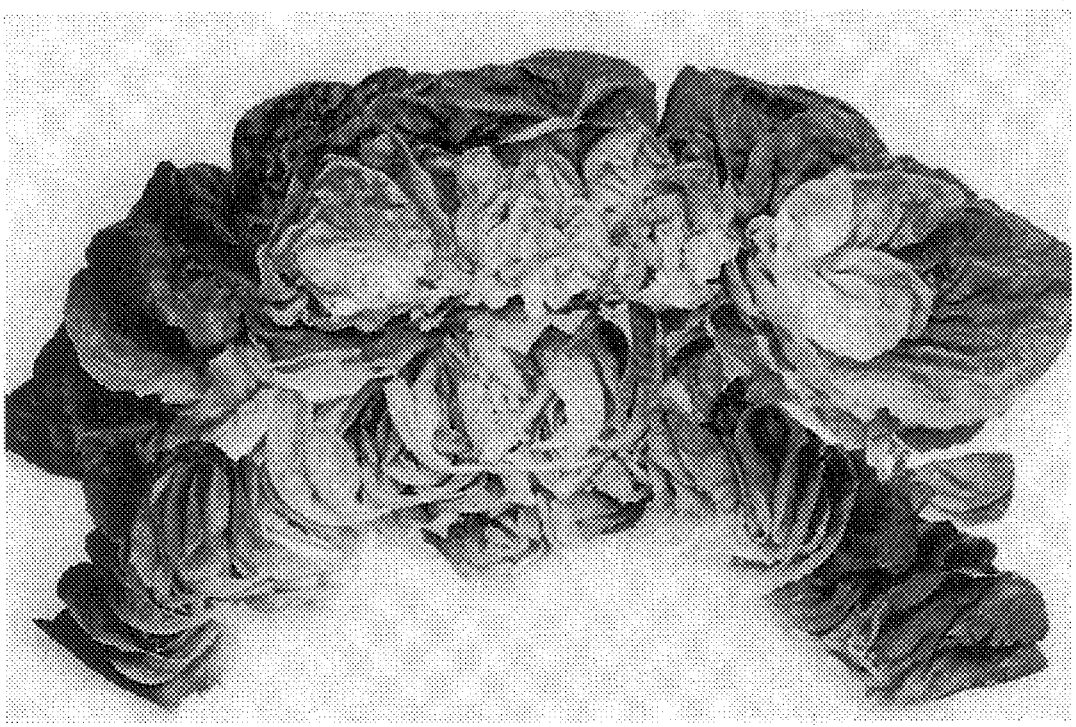
FIG. 7 shows a comparison between the removed leaves of a head of butterhead lettuce (top) and a head of multileaf butterhead lettuce according to the invention (below).

The present invention will be illustrated with reference to the accompanying examples.

EXAMPLE 1

Obtaining Butterhead Lettuce Plants with Multileaf Characteristic

A hybridization was made (designated with the number 5358) between two lettuce plants of the butterhead lettuce type. This was a hybridization between two selection lines of applicant. The mother had code 16487 and the father had F4[1366 OPG×F2 (15336×Troppo×1600×Bizet)].

In the F2 of this hybridization a plant was found a year later with features such as the plant of the invention. Seed was recovered from this plant and this seed was sown the following year in order to assess the external features on a larger number of progeny plants. Of —these F3 plants a number of plants were selected once again on the basis of the combination of (new) phenotype according to the invention and other quality-determining features (leaf thickness, leaf shape, leaf colour, head shape, head structure, yield, resistance to downy mildew, etc.).

This process of line selection was continued in the following 10 years, and a pure line was thus obtained (designated with the number 5338). This line is a good combination of a new phenotype according to the invention and the other quality-determining features.

For a further improvement of the phenotype of the plants of the invention, this line was crossed two years later with the variety S0256. In the progeny of this hybridization a rigorous selection was once again made from the F2 for plants with a very large number of leaves of substantially equal dimensions, combined with attractive leaf and head features and other features desirable for the culture of lettuce. After plant selection in the F2 and line selection from the F3 generation, a sufficiently pure line was finally obtained three years later, which is designated with the number RZ 97.41561, and seed of which was deposited on 1 April 1997 at The National Collections of Industrial and Marine Bacteria Limited (23 St. Machar Drive, Aberdeen AB2 1RY, Scotland, UK) under number NCIMB 40877 in order to illustrate the invention.

EXAMPLE 2

Decree of Expression and Inheritance of the Multileaf Characteristic

Plants of several standard varieties of the butterhead lettuce type for greenhouse culture (Floris RZ, Vegas RZ and Limit RZ), of two multileaf lines (No 5338 and RZ 97.41561) and of an F2 between a normal butterhead lettuce line and the multileaf line No 5338 were sown and further cultivated. The cultivation took place under a standard cultivation regime for greenhouse lettuce. The observations are an average of 4 plants per variety or line. The plants were prepared as for auction before assessment, i.e. old leaves with deposits or yellowed leaves were removed.

TABLE 1

Average head weight in grams (± SE), number of leaves (N) with a leaf length greater than 4 cm distributed over a number of length classes (± SE), and the quotient of the average head weight and the total number of leaves longer than 4 cm (± SE) of three butterhead lettuce varieties (not multileaf) and two multileaf lines

| Variety/line | Multileaf ? | WEIGHT (grams) | N 4–8 cm | N 8–12 cm | N 12–16 cm | N > 16 cm | Ntotal (>4 cm) | % in size 4–12 cm | WEIGHT/Ntotal |
|---|---|---|---|---|---|---|---|---|---|
| Floris RZ | no | 383 + 33 | 7.8 | 9.8 | 16.5 | 0.0 | 34.0 ± 3.1 | 52 | 11.3 ± 0.33 |
| Vegas RZ | no | 464 ± 80 | 8.8 | 8.5 | 21.5 | 5.0 | 43.7 ± 4.6 | 40 | 10.6 ± 0.94 |
| Limit RZ | no | 410 ± 34 | 19.8 | 10.5 | 23.3 | 5.8 | 59.2 ± 5.6 | 51 | 6.9 ± 0.84 |
| No 5338 | yes | 419 ± 39 | 44.8 | 43.5 | 50.5 | 0.0 | 138.8 ± 25.3 | 68 | 3.0 ± 0.25 |
| RZ 97.41561 | yes | 430 ± 29 | 168.0 | 87.8 | 19.5 | 0.0 | 275.3 ± 35.2 | 93 | 1.6 ± 0.18 |

Table 1 illustrates the differences which can be found in commercial (non-multileaf) butter lettuce varieties for the number of leaves longer than 4 cm: Floris RZ has relatively few leaves, the variety Limit RZ has almost twice as many in the category longer than 4 cm. The variety Limit RZ was included in this experiment because it was known that this variety forms relatively many leaves. However, the multileaf line No 5338 has more than twice as many leaves in the measured category than Limit RZ, and the line RZ 97.41561 even has four times as many. This increase in the number of leaves is accompanied by a sharp increase (both absolutely and in percentage terms) of leaves in the length category of 4–12 cm and a sharp decrease in the average weight per leaf.

76 plants of the F2 (butterhead lettuce×No 5338) were assessed. The butterhead lettuce which was used for crossing closely resembled Vegas RZ in respect of morphology. Table 2 gives the frequency distribution for the number of leaves longer than 4 cm per head of lettuce. Table 3 shows the frequency distribution for the quotient of the head weight and the number of leaves longer than 4 cm.

TABLE 2

Frequency distribution for the number of leaves longer than 4 cm of 76 plants of an F2 population from a hybridization between a butterhead lettuce line (not multileaf) and No 5338 (multileaf).

| Class: number of leaves longer than 4 cm | Number of plants |
| --- | --- |
| <40 | 0 |
| 40–50 | 7 |
| 50–60 | 24 |
| 60–70 | 20 |
| 70–80 | 6 |
| 80–90 | 2 |
| 90–100 | 5 |
| 100–110 | 1 |
| 110–120 | 2 |
| 120–130 | 2 |
| 130–140 | 1 |
| 140–150 | 2 |
| 150–160 | 2 |
| 160–170 | 1 |
| >170 | 1 |
| >Total | 76 |

TABLE 3

Frequency distribution of the quotient of the head weight and the number of leaves longer than 4 cm of 76 plants of an F2 population from a hybridization between a butterhead lettuce line (not multileaf) and No 5338 (multileaf).

| Class: Head weight/Number of leaves > 4 cm | Number of plants |
| --- | --- |
| <3.0 | 0 |
| 3.0–3.5 | 8 |
| 3.5–4.0 | 2 |
| 4.0–4.5 | 5 |
| 4.5–5.0 | 2 |
| 5.0–5.5 | 2 |
| 5.5–6.0 | 2 |
| 6.0–6.5 | 0 |
| 6.5–7.0 | 1 |
| 7.0–7.5 | 5 |
| 7.5–8.0 | 11 |
| 8.0–8.5 | 16 |
| 8.5–9.0 | 12 |
| 9.0–9.5 | 8 |
| 9.5–10.0 | 2 |
| >10 | 0 |
| Total | 76 |

Table 2 shows that the number of leaves larger than 4 cm per plant has a continuous distribution with a peak at 50–60 leaves larger than 4 cm per plant and with 17 plants having more than 90 leaves larger than 4 cm. These latter 17 plants were all of the multileaf type. The fact that no discontinuous segregation of the multileaf characteristic was obtained may be because the plants differed mutually in plant size and weight. The average head weight of the F2 plants varied from 350 to 655 g. In contrast to the number of leaves per plant, the quotient of head weight and number of leaves does give a discontinuous distribution, with 21 plants having a quotient smaller than 6.0 (all of the multileaf type) and 55 plants having a quotient greater than 6.5 (all of the normal type). The segregation corresponds with a monogenic recessive inheritance of the multileaf characteristic.

Within the group of plants of the multileaf type a further segregation was found, which indicates that the degree to which a plant has the multileaf characteristic is also determined by other genes. This is also supported by the fact that it was possible, starting from line No 5338 (an average of 139 leaves longer than 4 cm, see Table 1), to obtain a line via hybridization and specific selection having an average of 275 leaves longer than 4 cm (RZ 97.41561, see Table 1).

EXAMPLE 3

Obtaining Lamb's Lettuce Plants with Multileaf Characteristic

In the same manner as described in Example 1 a hybridization was made between two lettuce plants of the lamb's lettuce type. The selection of plants according to the invention and further obtaining of a pure line can likewise be realized in similar manner.

Seed of this line, which is designated with the number RZ 98.44080, was deposited on Jul. 15, 1998 at The National Collections of Industrial and Marine Bacteria Limited (23 St. Machar Drive, Aberdeen AB2 1RY, Scotland, UK) under number NCIMB 40960 in order to illustrate the invention.

It was found from hybridizations of the plants according to the invention with "normal" lamb's lettuce plants and selection of lines that the multileaf characteristic is inherited recessively and is genetically stable. The characteristic is expressed only at a later stage of the growth. In the initial stage of growth there are no differences between the type according to the invention and "normal" lamb's lettuce. The final leaf size is found to be smaller in the type according to the invention than in the "normal" type. The size of plants according to the invention is however comparable to "normal" lamb's lettuce plants. It was found from counts (see also Table 4) that 30 to 70 leaves are formed in "normal" plants, while this number varies between 130 and 210 leaves in plants according to the invention.

TABLE 4

Number of leaves per type

| "normal" lamb's lettuce plant | number of leaves | lamb's lettuce plant according to the invention | Number of leaves |
| --- | --- | --- | --- |
| 1 | 50 | 1 | 160 |
| 2 | 27 | 2 | 154 |
| 3 | 33 | 3 | 188 |
| 4 | 37 | 4 | 204 |
| 5 | 50 | 5 | 172 |
| 6 | 61 | 6 | 160 |
| 7 | 37 | 7 | 210 |
| 8 | 42 | 8 | 160 |
| 9 | 70 | 9 | 170 |
| 10 | 42 | 10 | 130 |

What is claimed is:

1. A lettuce seed designated RZ 97.41561 having NCIMB number 40877.

2. A lettuce plant or its parts produced by the seed of claim 1.

3. The plant of claim 2 wherein the plant has a multileaf trait.

4. A lettuce plant having all the morphological and physiological characteristics of the plant of claim 2.

5. A lettuce seed produced from the plant of claim 2.

6. A method for producing first generation hybrid lettuce seed comprising crossing a first parent lettuce plant with a second parent lettuce plant, wherein said first or second parent lettuce plant is the plant designated RZ 97.41561 having NCIMB number 40877, to produce first generation lettuce seed.

7. Seed produced by the method of claim 6.

* * * * *

UNITED STATES PATENT AND TRADEMARK OFFICE
Certificate

Patent No. 6,320,104 B1            Patented: November 20, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Cornelis Marinus Moor, Monster, Netherlands.

Signed and Sealed this Thirtieth Day of September 2003.

AMY J. NELSON
*Supervisory Patent Examiner*
Art Unit 1638